United States Patent
Goskonda et al.

(10) Patent No.: US 8,741,341 B2
(45) Date of Patent: Jun. 3, 2014

(54) MANUFACTURING AND PACKAGING ROOM TEMPERATURE STABLE DRONABINOL CAPSULES

(71) Applicant: Insys Therapeutics, Inc., Phoenix, AZ (US)

(72) Inventors: Venkat Goskonda, Phoenix, AZ (US); Ashok Chavan, Chandler, AZ (US); Kiran Amancha, Chandler, AZ (US); Scott Crisman, Chandler, AZ (US); Crystal Lopez, Goodyear, AZ (US)

(73) Assignee: INSYS Therapeutics, Inc., Chandler, AZ (US)

( * ) Notice: Subject to any disclaimer, the term of this patent is extended or adjusted under 35 U.S.C. 154(b) by 0 days.

(21) Appl. No.: 13/847,875

(22) Filed: Mar. 20, 2013

(65) Prior Publication Data
US 2013/0296415 A1    Nov. 7, 2013

Related U.S. Application Data

(60) Provisional application No. 61/643,713, filed on May 7, 2012.

(51) Int. Cl.
*A61K 9/64* (2006.01)
*A61K 9/66* (2006.01)
*A61K 9/68* (2006.01)

(52) U.S. Cl.
USPC .................. 424/451; 424/454; 424/455

(58) Field of Classification Search
None
See application file for complete search history.

(56) References Cited

U.S. PATENT DOCUMENTS

2009/0169586 A1 *   7/2009   Tracton .................. 424/400

FOREIGN PATENT DOCUMENTS

WO    WO 2006063109 A2 *   6/2006

* cited by examiner

*Primary Examiner* — Susan Tran
(74) *Attorney, Agent, or Firm* — Wood, Phillips, Katz, Clark & Mortimer

(57) ABSTRACT

The invention provides a method of manufacturing and packaging a room temperature stable cannabinoid dosage in an oil-based carrier, wherein the method employs the use of blister packaging and an inert gas atmosphere during blister packaging. The invention also provides a room temperature stable cannabinoid dosage prepared by the methods of the invention.

10 Claims, No Drawings

MANUFACTURING AND PACKAGING ROOM TEMPERATURE STABLE DRONABINOL CAPSULES

FIELD OF INVENTION

The present invention relates to a method of manufacturing and packaging a room temperature stable cannabinoid dosage in an oil-based carrier.

BACKGROUND OF THE INVENTION

Delta-9-Tetrahydrocannabinol (also known as THC, dronabinol and Δ9-THC) is a naturally occurring compound and is the primary active ingredient in the controlled substance marijuana. Marijuana refers to the dried flowers and leaves of *Cannabis Sativa*, the hemp plant. These parts of the plant contain several compounds called cannabinoids (including dronabinol), that may help patients with certain disease conditions.

Currently, dronabinol is commercially available in the U.S. as a sesame oil solution in a soft gelatin capsule under the tradename Marinol® from Unimed Pharmaceuticals, Inc., which is orally administered. Upon oral administration, the gelatin dissolves, releasing the drug. The dronabinol dissolved in sesame oil is then absorbed during its passage through the gastrointestinal tract. The Marinol® soft gelatin capsule form of dronabinol is highly unstable at room temperature, and it is required that the product be stored at refrigerated (2-8° C.) or cool (8-15° C.) conditions (Marinol® package label, Physicians Desk Reference®, ed. 2003). Additionally, Marinol® should be packaged in a well-closed container.

The need to store Schedule III Dronabinol product in a refrigerator is a major disadvantage for a pharmaceutical product. Accordingly, there is a need for developing a room temperature stable Dronabinol product that addresses problems associated with the storage of a Drug Enforcement Agency (DEA) Scheduled product (i.e., a controlled substance) at refrigerated conditions and patient convenience.

SUMMARY OF THE INVENTION

The present invention is directed to a method of manufacturing and packaging a cannabinoid dosage to achieve cannabinoid dosage stability at room-temperature.

In one embodiment, the invention provides a method of manufacturing and packaging a cannabinoid dosage, said method comprising utilizing a closed packaging unit like blister packaging the final pharmaceutical product.

In a preferred embodiment, the method comprises the following steps:
a) preparing a fill solution with a desired concentration of a cannabinoid;
b) encapsulating said fill solution in capsules; and
c) packaging said capsules in a packaging system.

In a preferred embodiment, the invention provides the method comprises the following steps:
a) preparing a fill solution with a desired concentration of a cannabinoid, comprising the following steps:
  i) heating an oil-based carrier in a first container to 40° C. or above under normal atmospheric conditions or under vacuum or an inert gas atmosphere;
  ii) de-aerating the oil-based carrier under vacuum;
  iii) heating a cannabinoid in a second container under vacuum or inert atmosphere until said cannabinoid liquefies to produce a liquefied cannabinoid;
  iv) transferring said liquefied cannabinoid from said second container to said first container;
  v) mixing said liquefied cannabinoid with said oil-based carrier until a solution becomes homogenous, (wherein the oil-based carrier is continuously flushed with said inert gas during the mixing);
  vi) adjusting the amount of said oil-based carrier to arrive at said desired cannabinoid concentration;
b) encapsulating said fill solution in capsules; and
c) packaging said capsules in a packaging system which comprises blister units or any closed packaging unit preferably under vacuum or an inert gas atmosphere.

In a preferred embodiment, the packaging step comprises continuously purging the packaging system with an inert gas.

In a preferred embodiment, the cannabinoid is dronabinol.

In another preferred embodiment, the inert gas is selected from nitrogen, argon, helium, krypton, neon, radon and xenon, but preferably nitrogen.

In another preferred embodiment, the desired capsules are soft gelatin capsules.

In another preferred embodiment, the oil-based carrier is sesame oil.

In some embodiments, the desired concentration of a cannabinoid is about 1-10% w/w (weight relative to the total weight of the formulation).

The invention also provides a cannabinoid dosage prepared by the methods of the invention.

DETAILED DESCRIPTION OF THE INVENTION

The present invention is directed to a method of manufacturing and packaging a cannabinoid dosage to achieve cannabinoid dosage stability at room-temperature.

In one embodiment, the invention provides a method of manufacturing and packaging a cannabinoid dosage.

In a preferred embodiment, the method comprises the following steps:
a) preparing a fill solution with a desired concentration of a cannabinoid;
b) encapsulating said fill solution in capsules; and
c) packaging said capsules in a packaging system which comprises blister units or any closed packaging unit under normal atmospheric conditions or under vacuum or an inert gas atmosphere.

In a more preferred embodiment, the invention provides the method comprises the following steps:
a) preparing a fill solution with a desired concentration of a cannabinoid, comprising the following steps:
  i) heating an oil-based carrier in a first container to 40° C. or above under vacuum or an inert gas or heating under normal atmospheric conditions.
  ii) de-aerating the oil-based carrier under vacuum;
  iii) heating a cannabinoid in a second container under vacuum or inert atmosphere until said cannabinoid liquefies to produce a liquefied cannabinoid;
  iv) transferring said liquefied cannabinoid from said second container to said first container;
  v) mixing said liquefied cannabinoid with said oil-based carrier until a solution becomes homogenous; and
  vi) adjusting the amount of said oil-based carrier to arrive at said desired cannabinoid concentration;
b) encapsulating said fill solution in capsules; and
c) packaging said capsules in a packaging system which comprises blister units or any closed packaging unit under a vacuum or an inert gas atmosphere.

In a more preferred embodiment, the packaging step comprises continuously purging the packaging system with an inert gas.

For purposes of the present invention, the term "cannabinoid" includes naturally occurring and non-natural derivatives of cannabinoids which can be obtained by derivatization of natural cannabinoids and which are unstable like natural cannabinoids. In other words, the cannabinoid used in the formulations of the invention may be natural, semi-synthetic, or synthetic. The cannabinoid may be included in its free form, or in the form of a salt; an acid addition salt of an ester; an amide; an enantiomer; an isomer; a tautomer; a prodrug; a derivative of an active agent of the present invention; different isomeric forms (for example, enantiomers and diastereoisomers), both in pure form and in admixture, including racemic mixtures; enol forms. The term "cannabinoid" is also meant to encompass derivatives that are produced from another compound of similar structure by the replacement of, e.g., substitution of one atom, molecule or group by another. The term "cannabinoid", as used in the present invention, includes, inter alia, delta-8tetrahydrocannabinol, delta-9-tetrahydrocannabinol, cannabidiol, cannabinol, cannabigerol, nabilone, delta-9-tetrahydro cannabinotic acid, the nonpsychotropic cannabinoid 3-dimethylnepty II carboxylic acid homologine 8, delta-8-tetrahydrocannabinol. (1. Med. Chem. 35, 3135, 1992), prodrugs of cannabinoids, as well as pharmaceutically acceptable salts and complexes of cannabinoids.

The term inert gases included but are not limited to noble gases and nitrogen. Noble gases include but are not limited to helium, neon, argon, krypton, xenon and radon. In a preferred embodiment, the inert gas is nitrogen.

In a preferred embodiment, the cannabinoid is dronabinol.

Preparation of a Fill Solution

First, a cannabinoid fill solution is prepared.

A required amount of an oil-based carrier is weighed and transferred to a first container (also referred to as a "mixing tank"). In certain embodiments, the oil-based carrier is selected from the group consisting of soybean oil, olive oil, cotton seed oil, peanut oil, sesame oil, castor oil, and mixtures of any of the foregoing. In a preferred embodiment, the oil-based carrier is sesame oil (e.g., a food grade, NF grade, Ph.Eur grade, or JP grade sesame oil). In a preferred embodiment, the sesame oil is super refined and contains a stabilizer such as butylatedhydroxytoulene.

In some embodiments, the desired concentration of a cannabinoid as the active pharmaceutical ingredient (API) is about 1-6% w/w, to produce capsules containing 2.5 mg, 5 mg and 10 mg cannabinoid respectively, wherein the weight is based on the total solution. Preferably, the API concentration of the capsules prepared in accordance with the provided methods ranges from about 1-10% w/w or more particularly 1.5% w/w-6.5 % w/w.

Then, the oil-based carrier in the first container is heated to 40° C. and above under normal atmospheric conditions or vacuum or inert gas.

In a second container, a cannabinoid is heated until the cannabinoid liquefies to produce a liquefied cannabinoid.

Once the cannabinoid is liquefied, it is transferred to the first container containing the warm oil-based carrier. The cannabinoid and the oil-based carrier are mixed until the solution becomes homogenous.

After the mixing of the API with the oil-based carrier, the amount of oil-based carrier required for the desired concentration of the cannabinoid is calculated, the required amount of oil-based carrier is added to the contents of the mixing container, and the solution is mixed until it becomes homogenous.

Encapsulation

The dosage fill solution prepared as described above is then fed into an encapsulation machine, where the solution is encapsulated to capsules. Preferably, the capsules are soft gelatin capsules.

In a preferred embodiment, the produced capsules are transferred from the encapsulation machine to the rotary tumbler by a conveyor. The capsules are dried in rotary tumbler followed by drying in environmentally controlled drying tunnels. At the completion of the drying step, the capsules are visually inspected for any defects, transferred from shallow trays to deep holding trays and washed.

Packaging

Finally the capsules are packaged in a packaging system which comprises a closed system (e.g. blister or any enclosed packaging system) under normal atmospheric condition, under vacuum or inert gas atmosphere.

There are many ways in which the skilled in the art may practice the packaging step. The description below refers to only some embodiments of the invention and is not limiting in any way.

Preferably, to prepare to package the capsules, the packaging equipment is set-up in advance.

A Nitrogen Flush system is set up. For purposes of the present invention, the Nitrogen Flush system refers to a system wherein a nitrogen atmosphere is maintained in the blister packaging machine at the place where the top and bottom blister materials come together. Nitrogen is applied through a block which is connected to a nitrogen tank placed outside the blister packaging machine. Preferably, nitrogen is supplied at a pressure of above 0.01 p.s.i. (pounds per square inch) and preferably between about 0.1 to about 5 psi.

In a preferred embodiment, a sensor that checks for correct placement of capsules in each cavity of blister package is placed in the packaging machine. The sensor may be connected to a computer. However, alternative mechanisms may be used to monitor for correct placement.

Once the set-up is complete, the cannabinoid capsules are poured into trays. The capsules are transferred from the trays to blister packaging machine by a conveyor. The capsules are then sealed in a blister package at predetermined operating conditions (eg: speed, temperature etc.). Preferably, leak and fiber optic light tests are performed on empty blister units prior to packaging the capsules.

The capsules may be arranged in any configuration.

The blister units are preferably, continuously flushed with the inert gas or maintained under vacuum so that the capsules are sealed from atmospheric air. As each blister unit comes off the machine, it is inspected for damaged cavities and clear and legible print on at least one cavity for each blister unit. Preferably, blister units that pass the inspection are bulk packed into corrugated shipper.

In a preferred embodiment, an in-process inspection is performed on packaged capsules.

The presently provided methods provide cannabinoid capsules which are stable at room temperature for at least twelve to eighteen months.

The invention also provides a cannabinoid dosage prepared by the methods of the invention.

Cannabinoid Stability Data

Tables 1 and 2 include stability data for the dronabinol dosage of the present invention. The dronabinol dosage of the present invention was stored at accelerated temperature and humidity condition [40 degrees C./75% relative humidity (RH)] for six months to assess stability of the product at room temperature. As a control, dronabinol dosage packaged in bottles and dronabinol dosage packaged in blisters without the use of the nitrogen gas flush were stored and tested for stability. The extent of degradation (potency and impurities) was measured at production (zero time) and then one, two, three and six months during stability storage. Percent potency and percent total impurities (Tables 1 and 2) were determined by HPLC/UV analysis. As shown in tables 1 and 2, the nitrogen flushed blister-packaged dronabinol dosage of the present invention was stable and did not show any significant change in potency or individual and total impurities. However, the two control dosages (dronabinol dosage packaged in bottles and dronabinol dosage packaged in blisters without the use of the nitrogen gas flush) showed significant degradation during the 3 and 6-month storage at accelerated temperature and humidity conditions. The nitrogen flushed blister-packaged dronabinol dosage, 2.5, 5 and 10 mg dosage strengths, of the present invention maintained its potency (assay) within about 1% of the label claim compared to 3-7% loss for two control dosages. The total impurity levels for two control dosages were 2-3 times higher than the nitrogen gas flushed blister packaged product when stored at 40° C./75% RH (accelerated stability storage conditions). The stability study demonstrated that stability of dronabinol dosage is improved significantly with the utilization of enclosed packaging system with the use of nitrogen gas flush.

The present invention has been described by reference to some of its preferred embodiments. This description is, however, in no way meant to limit the scope of the invention. Other embodiments that do not depart from the spirit of the invention should be similarly encompassed and addressed by the aforementioned description and subsequent claims. So for example, dronabinol formulations/dosages in liquid solutions, soft gelatin capsules or hard gelatin capsules or tablets like those disclosed in U.S. Pat. No. 8,222,292 and U.S. Patent Application Publication 2006/060888 (which are incorporated by reference herewith) could be packaged in accordance with this invention to enable room temperature stability for at least one year.

What is claimed is:

1. A method of manufacturing and packaging a cannabinoid dosage, consisting of the following steps:
    a) preparing a fill solution with a desired concentration of a cannabinoid in a liquid carrier;
    b) encapsulating said fill solution in capsules;
    c) packaging said capsules in a closed packaging system; and
    d) removing atmospheric air from the capsules,
wherein the removing of atmospheric air consists solely of purging said packaging system with an inert gas, and wherein said packaging system provides a room temperature stable product.

TABLE 1

Stability of Dronabinol Capsules at 40° C. ± 2° C./75% ± 5% RH
Dronabinol Capsules USP

|  |  | Bottled Product | | | | | Blister Packaged Product with Nitrogen | | | | |
| --- | --- | --- | --- | --- | --- | --- | --- | --- | --- | --- | --- |
|  |  | T0 | 1 month | 2 month | 3 month | 6 month | T0 | 1 month | 2 month | 3 month | 6 month |
| 2.5 mg | Assay | 104.0 | 102.8 | 96.7 | 84.7 | 97.2 | 103.7 | 103.6 | 103.4 | 102.6 | 102.4 |
|  | Total Impurities | 1.7 | 2.4 | 5.7 | 12.1 | 6.7 | 1.7 | 1.9 | 1.8 | 1.8 | 2.4 |
| 5 mg | Assay | 103.3 | 102.6 | 100.4 | 95.7 | 97.3 | 103.6 | 103.3 | 103.2 | 102.6 | 100.5 |
|  | Total Impurities | 2.2 | 3.1 | 4.2 | 7.5 | 6.9 | 2.1 | 2.3 | 2.5 | 2.3 | 2.4 |
| 10 mg | Assay | 102.7 | 101.1 | 99.6 | 95.5 | 97.8 | 101.2 | 101.0 | 101.4 | 100.3 | 100.7 |
|  | Total Impurities | 2.1 | 2.6 | 4.2 | 5.8 | 5.5 | 1.8 | 2.0 | 2.1 | 2.1 | 2.3 |

TABLE 2

Stability of Dronabinol Capsules at 40° C. ± 2° C./75% ± 5% RH
Dronabinol Capsules USP

|  |  | Blister Packaged Product without Nitrogen | | | | Blister Packaged Product with Nitrogen | | | | |
| --- | --- | --- | --- | --- | --- | --- | --- | --- | --- | --- |
|  |  | T0 | 1 month | 2 month | 3 month | T0 | 1 month | 2 month | 3 month | 6 month |
| 2.5 mg | Assay | 101.5 | 100.5 | 97.5 | 94.9 | 103.7 | 103.6 | 103.4 | 102.6 | 102.4 |
|  | Total Impurities | 2.1 | 3.1 | 4.4 | 5.5 | 1.7 | 1.9 | 1.8 | 1.8 | 2.4 |
| 5 mg | Assay | 101.8 | 102.3 | 99.9 | 99.5 | 103.6 | 103.3 | 103.2 | 102.6 | 100.5 |
|  | Total Impurities | 2.1 | 2.6 | 3.8 | 4.5 | 2.1 | 2.3 | 2.5 | 2.3 | 2.4 |
| 10 mg | Assay | 101.2 | 100.9 | 98.9 | 99.1 | 101.2 | 101.0 | 101.4 | 100.3 | 100.7 |
|  | Total Impurities | 2.1 | 2.8 | 3.6 | 4.5 | 1.8 | 2.0 | 2.1 | 2.1 | 2.3 |

2. The method of claim 1, wherein the packaging system is a blister package.

3. The method of claim 2 wherein the blister package is constructed of material that minimizes exposure to moisture and air.

4. The method of claim 1, wherein the cannabinoid is dronabinol.

5. The method of claim 1, wherein the liquid carrier is oil-based carrier.

6. The method of claim 5, wherein the oil-based carrier is sesame oil.

7. The method of claim 1, wherein the capsules are soft gelatin capsules.

8. The method of claim 1, wherein the inert gas is nitrogen.

9. The method of claim 1, wherein the desired cannabinoid concentration is about 1-10% w/w.

10. The method of claim 9 wherein the desired concentration is about 1.5-6.5% w/w.

\* \* \* \* \*